United States Patent [19]

Verde

[11] Patent Number: 4,985,257

[45] Date of Patent: Jan. 15, 1991

[54] HEMORRHOIDAL TREATMENT AND COMPOSITION

[76] Inventor: Giancarlo U. Verde, 9, Via Siria, 00184 Roma, Italy

[21] Appl. No.: 386,726

[22] Filed: Jul. 31, 1989

[30] Foreign Application Priority Data

Feb. 6, 1989 [IT] Italy ............................. 47616 A/89

[51] Int. Cl.$^5$ .............................................. A61K 33/04
[52] U.S. Cl. ..................................... 424/705; 424/713; 514/574; 514/882
[58] Field of Search ................ 424/705; 514/713, 574, 514/882

[56] References Cited

U.S. PATENT DOCUMENTS 4,225,587  9/1980  Hess .................................... 424/162
4,761,285  8/1988  Vasiliou ........................... 424/195.1

OTHER PUBLICATIONS

Handbook of Nonprescription Drugs, 5th ed, 1977, pp. 63-67.
Grieve, "A Modern Herbal", vol. 1, p. 111.
43, Chemical Abstracts, 3956g.
43, Chemical Abstracts, 3956h.
Merck Index, 10th Edition, pp. 1099, 1287-1289 (1983).
"Drug Topic Red Book", p. 554 (1987).
"Drug Topic Red Book" p. 658 (1989).
Harrison's "Principles of Internal Medicine", Anorectal Problems: Hemorrhoids, 10th Edition, pp. 1764-1765, (1983).
Physicians' Desk Reference, 41st Edition, p. 709 (1987).
Martindale's Pharmacopoeia, undated, p. 504.
Martindale's The Extra Pharmacopoeia, 1989, pp. 932-933.

Primary Examiner—Leonard Schenkman
Attorney, Agent, or Firm—Banner, Birch, McKie & Beckett

[57] ABSTRACT

A composition comprising between about 15 and 30 weight percent sulfur and between about 85 and 70 weight percent cream of tartar as active ingredients for reducing hemorrhoidal swelling and relieving hemorrhoidal symptoms. The invention also relates to method of relieving hemorrhoidal symptoms and reducing hemorrhoidal swelling by ingesting a therapeutically effective quantity of the composition.

11 Claims, No Drawings

HEMORRHOIDAL TREATMENT AND COMPOSITION

BACKGROUND OF THE INVENTION

1. Field of the Invention

This invention relates to a composition of matter for relieving hemorrhoidal symptoms and reducing hemorrhoidal swelling. The invention also relates to a method of reducing hemorrhoidal swelling and relieving hemorrhoidal symtoms by ingesting a therapeutically effective quantity of the composition.

2. Description of Related Arts

A hemorrhoid is an itching, often painful mass of dilated veins in swollen anal tissue. Hemorrhoids may be categorized as internal or external, depending upon whether the internal or the external hemorrhoidal plexus of veins is enlarged. Both types of hemorrhoids are common and are associated with increased pressure in the portal veinous system, such as during pregnancy and by straining during defecation.

Both internal and external hemorrhoids may be quite painful, although internal hemorrhoids typically are not painful until there exists thrombosis, infection, or erosion of the mucosal surface which overlies the hemorrhoid. Typically, any of these conditions results in bleeding, manifested as blood on the stool, and a feeling of vague anal discomfort, including pruritus and a burning sensation. An internal hemorrhoid may prolapse through the anus. Although the level of physical discomfort may not increase, one who suffers such a condition will be embarrassed by constant soiling of the underclothing. Further, a prolapsed hemorrhoid may become infected or thrombosed, and is susceptible to profuse bleeding upon defecation.

Hemorrhoids can be treated by sitz baths or other forms of moist heat, suppositories, stool softeners, and bed rest. Various commercially available preparations are intended to be applied to the hemorrhoid to relieve the pain and itch of swollen hemorrhoidal tissue, but such preparations do little to reduce hemorrhoidal swelling. Other compositions are designed to be ingested or to be applied to hemorrhoids which are externally accessible. One such composition, comprising Leptandra Culver's root, chick peas, and grape seed, is disclosed in U.S. Pat. No. 4,761,285. However, this composition is unsatisfactory because Leptandra Culver's root is described as a violent cathartic, possibly an emetic, when fresh. Fresh root also may produce bloody stools and possibly abortion. Internal hemorrhoids which have a low degree of prolapse or enlargement together with pruritus or intermittent bleeding can be treated by injection of sclerosing solution. Permanently prolapsed and external hemorrhoids are treated surgically.

SUMMARY OF THE INVENTION

It is an object of the invention to provide an edible composition of matter which relieves hemorrhoidal symptoms and reduces hemorrhoidal swelling.

It is a further object of the invention to provide an edible composition comprising sulfur and cream of tartar as active ingredients which relieve hemorrhoidal symptoms and reduce hemorrhoidal swelling.

It is another object of this invention to provide a method of relieving hemorrhoidal symptoms and reducing hemorrhoidal swelling.

It is a still further object of this invention to relieve hemorrhoidal symptoms and reduce hemorrhoidal swelling by ingesting a sulfur- and cream of tartar-containing medicament.

In accordance with these and other objects, the invention relates to a composition comprising between about 15 and 30 weight percent sulfur and between about 85 and 70 weight percent cream of tartar, based on the combined weight of sulfur and cream of tartar, as active ingredients for reducing hemorrhoidal swelling and relieving hemorrhoidal symptoms. The invention also relates to method of relieving hemorrhoidal symptoms and reducing hemorrhoidal swelling by ingesting a therapeutically effective quantity of this composition.

DETAILED DESCRIPTION OF THE INVENTION

This invention is based on the discovery that ingestion of a composition of matter comprising sulfur and cream of tartar as active ingredients relieves hemorrhoidal symptoms and reduces swelling of hemorrhoids. Ingestion of a therapeutically effective quantity of this composition relieves hemorrhoidal symptoms within a short period and reduces swelling of the hemorrhoids, thus reducing the likelihood of permanent prolapse of the hemorrhoid. The invention also is based on the discovery of a particular range of sulfur and cream of tartar in the composition of matter which, when ingested, relieves hemorrhoidal symptoms and reduces swelling in the hemorrhoid, yet does not produce any undesirable side effects.

The composition of matter this invention comprises sulfur and cream of tartar as the sole necessary therapeutically active ingredients to relieve hemorrhoidal symptoms and reduce swelling of the hemorrhoids. Depending upon the form in which the composition is made available to the user, pharmaceutically and physiologically unobjectionable adjuvants such as extenders, bulking agents, flavoring and coloring agents (whether natural or artificial), and emulsifiers or suspending agents, as described below, may, of course, be present with sulfur and cream of tartar in the composition. However, these adjuvants form no part of this invention.

The composition of the invention comprises between 15 and 30 weight percent sulfur and between about 85 and 70 weight percent cream of tartar, based on the combined weight of sulfur and cream of tartar. Preferably, the composition comprises of between about 20 and 30 weight percent sulfur and between about 80 and 70 weight percent cream of tartar, and more preferably contains about 25 weight percent sulfur and about 75 weight percent cream of tartar.

Both cream of tartar and sulfur are solids at ambient conditions, i.e., at a temperature between about 0° C. and 50° C. Cream of tartar also is known by a variety of names, including potassium bitartrate, potassium hydrogen tartrate, and potassium acid tartrate. Cream of tartar exists as colorless crystals or as white crystalline powder. Cream of tartar is soluble in water at a concentration of about 0.4 weight percent at a temperature of about 10° C. to about 6% at 100° C. Sulfur is available in a variety of forms, each of which is a crystalline powder suitable for use in the practice of this invention. However, it is preferred that the forms of sulfur commonly called "pharmaceutical sulfur," i.e., sublimed sulfur ("flowers of sulfur"), washed sulfur, and precipitated sulfur ("milk of sulfur"), be utilized. More preferably, sublimed sulfur is utilized as an active ingredient in the composition of this invention. Sulfur is not soluble in water. Neither sulfur nor cream of tartar is soluble in alcohol.

The form in which the edible composition is supplied to the consumer is not critical and forms no part of the invention. Because the composition is a mixture of two solid, crystalline powders, the composition conveniently is supplied as a homogeneously blended powder of the desired proportion of sulfur and cream of tartar, together with any adjuvants. However, the homogeneously blended powder could be combined with binding agents and formed into pills, tablets, and the like. Shaped, compressed articles such as pills and tablets also may be coated. Similarly, the powder could be inserted into capsules made of known materials such as gelatin. Such capsules are known to those in the art.

Because sulfur is a pale yellow to yellow powder and cream of tartar is a colorless white crystal and comprises the major fraction of the composition, the composition of the invention in blended powder form typically would be a light yellow compound. The composition of the invention is not completely soluble in water, but, with agitation, will form a suspension which is sufficiently stable for a period which is relatively short, but sufficient to drink the suspension. The taste of the composition in water is not unpleasant. However, if desired, flavorings may be added. Coloring agents may also be added if desired.

In accordance with the method of the invention, a therapeutically effective quantity of the composition is ingested when symptoms of hemorrhoidal suffering are experienced. Typically, a therapeutically effective quantity is a daily dose of between about 20 and 60 grams of powdered composition consisting solely of ingredients active in the reduction of hemorrhoidal swelling and relieving hemorrhoidal symptoms, i.e., sulfur and cream of tartar. Preferably, between about 25 and 45 grams and, more preferably, between about 25 and 35 grams, are ingested daily. The dosage may be adjusted by the user to accommodate differences (for example, body weight, severity of the symptoms) among individuals. Preferably, about half of the therapeutically effective dosage is taken twice daily, preferably at approximately twelve hour intervals. Treatment is continued until completed relief of hemorrhoidal symptoms and reduction of hemorrhoidal swelling has been achieved.

The specific gravity of the composition of the invention made by blending only sulfur powder and cream of tartar powder typically will be between about 1.60 and 2.25, more typically between about 1.75 and 2.10. Thus, the therapeutically effective volume of a composition of the invention consisting solely of powdered sulfur and cream of tartar typically is between about 10 and 35 cubic centimeters daily, and more typically between about 15 and 25 cubic centimeters daily.

The therapeutically effective dosage described herein considers only the weight of volume of the ingredients therapeutically active against hemorrhoidal swelling and symptoms of hemorrhoids, i.e., only sulfur and cream of tartar. Skilled practitioners recognize that adjuvants affect the weight of volume of the dosage and the quantity of pharmaceutically and physiologically unobjectable adjuvants may vary significantly between dosage types. For example, a pill or tablet compressed for ingestion without chewing typically will have little additional material, and may be significantly more dense than loose powder. Similarly, a therapeutically effective quantity of a powdered composition to which a large quantity of inert material such as flavoring (for example, sugar) and coloring agents has been added, will be not only greater in weight but also larger in volume than the active ingredients alone. However, adjustments of the dosage to account for the presence of adjuvants is within the skill of the suppliers of such products.

It has been discovered that ingestion of a therapeutically effective quantity of the composition of the invention, i.e., a composition consisting essentially of between about 15 and 30 weight percent sulfur and between 85 and 70 percent cream of tartar, based on the combined weight of sulfur and cream of tartar, quickly relieves the burning and itching of painful hemorrhoidal tissue. Not only does the compound promptly relieve these annoying symptoms, but also it subsequently reduces the swelling of the hemorrhoids, thus reducing the likelihood of thrombosis, erosion of the mucosa over the hemorrhoid, infection, and the likelihood that an internal hemorrhoid will become permanently prolapsed. Use of the product of the invention in accordance with the method of the invention causes reabsorption of existing prolapses. Further, ingestion of a medicament clearly is more convenient than application of greasy or oily compositions, such as known treatments, to the affected tissues, which typically are not externally visible. Typically, known products do not improve the user's condition by reducing swelling, but instead are merely anti-pruritic or analgesic.

The following examples are intended to illustrate the invention, and are not to be considered limiting in any way. The invention is limited only by the scope of the appended claims.

EXAMPLE 1

A composition consisting essentially of 25 grams of flowers of sulfur and 75 grams of cream of tartar is made by mixing the powdered sulfur and the cream of tartar until a homogeneous blend is obtained. At the onset of hemorrhoidal symptoms of burning and itching in the rectal region, 15 grams (about 12 cubic centimeters) of the composition described in this example is ingested together with about 4 ounces of water. The pain and itching are quickly relieved, and the swelling is subsequently reduced. A second dose is taken about 12 hours after the first is taken, if desired.

EXAMPLE 2

Fifteen grams of the composition described in Example 1 is mixed with about a 125 milliliters of spring water. A small fraction of the cream of tartar dissolves, but the remainder of the cream of tartar and all of the flowers of sulfur remain undissolved. However, with sufficient stirring, these particles remain suspended in the water for a period sufficient to drink the suspension to relieve hemorrhoidal symptoms and reduce hemorrhoidal swelling.

EXAMPLE 3

Fifteen grams of sulfur, 85 grams of cream of tartar, and about 70 grams of common sugar are mixed to form a homogeneous blend. When hemorrhoidal symptoms are experienced, about 40 grams of the mixture are admixed with about 200 milliliters of water. The sugar and a small quantity of cream of tartar dissolve, while the remaining cream of tartar and sulfur remain suspended in the water after stirring is stopped for a time sufficient to drink the suspension. A second equal quantity of powder is ingested as a second dose about 12 hours after the first ingestion. Hemorrhoidal symptoms are relieved quickly, and hemorrhoidal swelling is decreased.

Although preferred embodiments of this invention have been described herein, skilled practitioners recognize that changes and modifications may be made without departing from the spirit of the invention, as defined in and limited only by the scope of the appended claims.

I claim:

1. A composition of matter comprising as active ingredients for relieving hemorrhoidal symptoms and reducing hemorrhoidal swelling between about 15 and 30 weight percent sulfur and between about 85 and 70 weight percent cream of tartar, based on the combined weight of sulfur and cream of tartar.

2. The composition claim 1 comprising between 20 and 30 weight percent sulfur and between about 80 and 70 weight percent cream of tartar.

3. The composition of claim 2 comprising about 25 weight percent sulfur and 75 percent cream of tartar.

4. The composition of claim 1, further comprising pharmaceutically and physiologically unobjectionable adjuvants.

5. The composition of claim 2, further comprising pharmaceutically and physiologically unobjectionable adjuvants.

6. The composition of claim 3, further comprising pharmaceutically and a physiologically unobjectionable adjuvants.

7. A method for relieving hemorrhoidal symptoms and reducing hemorrhoidal swelling comprising ingesting after experiencing hemorrhoidal symptoms a therapeutically effective but non-laxative quantity of a composition comprising, as active ingredients for relieving hemorrhoidal symptoms and reducing hemorrhoidal swelling, between about 15 and 30 weight percent sulfur and between about 85 and 70 weight percent cream of tartar based on the combined weight of sulfur and cream of tartar.

8. The method of claim 7 wherein the therapeutically effective but non-laxative quantity is between about 20 and 60 grams of sulfur and cream of tartar daily.

9. The method of claim 8 wherein the therapeutically effective but non-laxative quantity of the composition is ingested in two approximately equal doses.

10. The method of claim 8 wherein the therapeutically effective but non-laxative quantity is between about 25 and 45 grams of sulfur and cream of tartar daily.

11. The method of claim 10 wherein the therapeutically effective but non-laxative quantity is ingested in two approximately equal doses.

* * * * *